United States Patent [19]

Meryman et al.

[11] Patent Number: 4,585,735
[45] Date of Patent: Apr. 29, 1986

[54] PROLONGED STORAGE OF RED BLOOD CELLS

[75] Inventors: Harold T. Meryman, Sandy Spring, Md.; Marne Hornblower, Washington, D.C.; Ralph Syring, Silver Spring, Md.

[73] Assignee: American National Red Cross, Washington, D.C.

[21] Appl. No.: 632,242

[22] Filed: Jul. 19, 1984

[51] Int. Cl.$^4$ .................. A01N 1/02; A61K 35/18
[52] U.S. Cl. .................................. 435/2; 424/101
[58] Field of Search ..................... 424/101; 435/2

[56] References Cited

U.S. PATENT DOCUMENTS

| 4,061,537 | 12/1977 | Seiler et al. | 435/2 |
| 4,356,172 | 10/1982 | Nakao et al. | 435/2 |
| 4,476,221 | 10/1984 | Kane et al. | 424/101 |

OTHER PUBLICATIONS

Chem. Abstracts, vol. 91, 33536m, published 1979.
Chem. Abstracts, vol. 79, 112,107c, published 1973.

Primary Examiner—Sam Rosen
Attorney, Agent, or Firm—Holman & Stern Chartered

[57] ABSTRACT

The present invention discloses a hypotonic suspension medium and a method for prolonged storage of red blood cells at about 4° C. The suspension medium comprises about 80–150 mM glucose, 30–80 mM mannitol, 6–90 mM potassium citrate, 1–5 mM adenine and 10–200 mM ammonium chloride or acetate in an aqueous solution having a pH of about 6.8 to 7.2 and an osmolarity of about 180–220 milli-osmolar. The suspension medium and the method of the present invention allow viable storage of red blood cells at about 4° C. up to 125 days or more.

10 Claims, 2 Drawing Figures

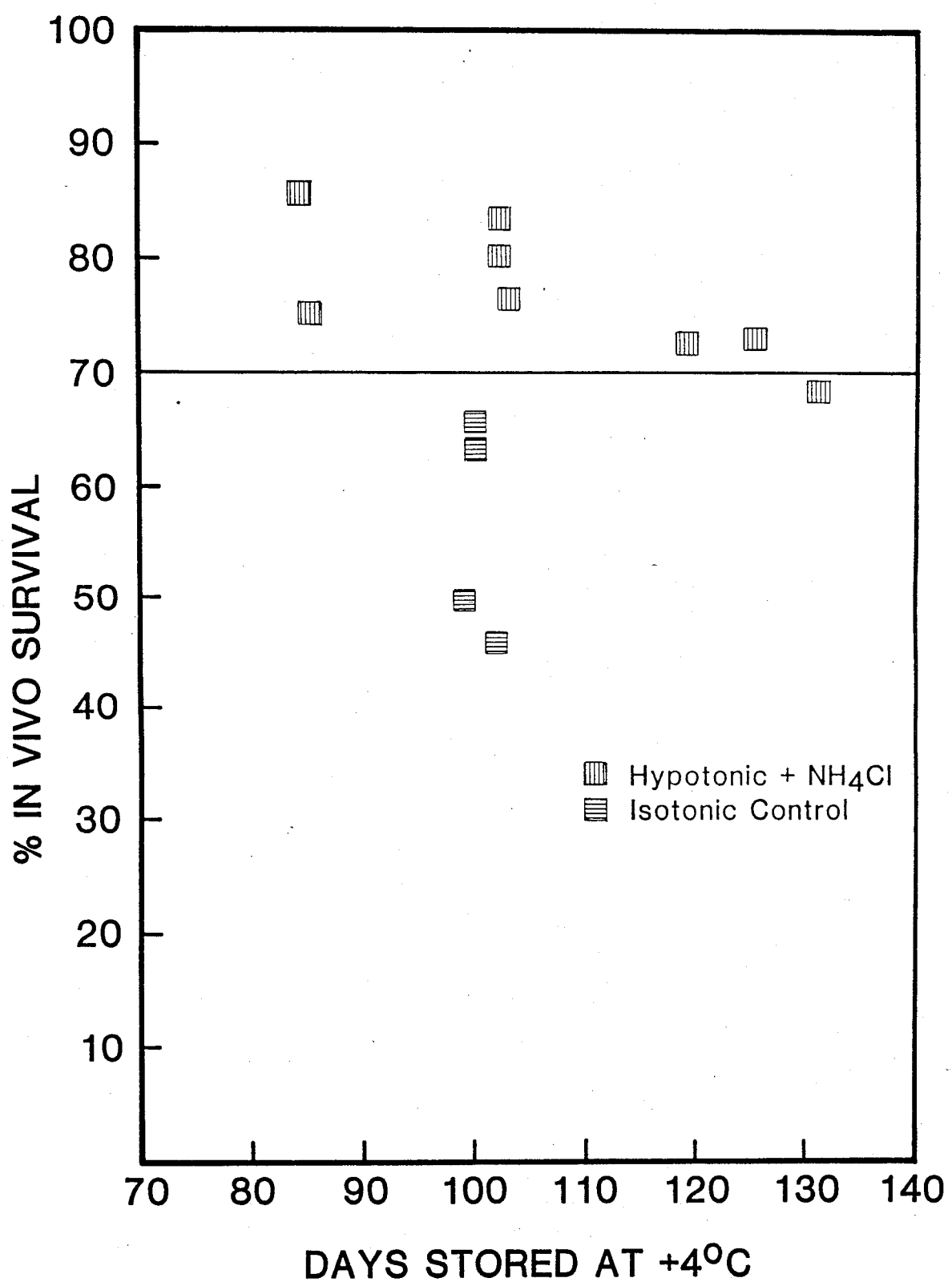

PROLONGED STORAGE OF RED BLOOD CELLS

BACKGROUND OF THE INVENTION

1. Technical Field

The present invention is related to preservation of red blood cells in substantially physiologically native state. More particularly, the present invention is related to a novel suspension medium for storage of human red blood cells at about 4° C. in a condition suitable for blood transfusion. The novel suspension medium of the present invention makes it feasible to substantially increase the storage time of the red blood cells than was heretofore possible.

2. Prior Art

Storage or preservation of red blood cells in a suspension medium at about 4° C. according to standard blood bank procedure is well known. As far as known to the Applicants there are no literature references reporting the effects of either of hypotonic suspension or of the additon of penetrating salts, e.g., ammonium salts as related to the keeping quality of red blood cells.

It has been observed, however, that, during continued refrigerated storage, human red cells undergo a shape change with the development of spicules which may ultimately bud off into small vesicles. This reduces the surface area of the red cell, presumably rendering it less flexible and less able to pass through the filtration system in the spleen. This in turn leads to the removal of cells from the circulation within a few minutes following transfusion. Acceptable standards for transfusable red cells require that at least 70% of the cells must still be circulating 24 hours following transfusion.

The present invention overcomes the limitations and problems associated with the prior art process. It was reasoned that increasing the surface tension of the cells by osmotic swelling would theoretically tend to forestall the development of spicules. Therefore, a suspension medium of suitable osmolarity and membrane permeability was developed which could preserve the red blood cells at 4° C. for extended period of time in a condition suitable for transfusion in accordance with standards established for transfusion of red blood cells (RBCs). It was discovered that inclusion of certain penetrating compounds, such as ammonium salts, preferably $NH_4Cl$ and $NH_4COOCH_3$, in a suspension medium not only avoids the deleterious effects of low ionic concentration, but also provides certain positive benefits as described more fully infra.

SUMMARY OF THE INVENTION

It is, therefore, an object of the present invention to provide a suspension medium for red blood cells which substantially increases the storage time of the suspended RBCs at about 4° C. while maintaining the transfusion quality of the stored RBCs.

It is a further object of the present invention to provide a method of storing RBCs for extended period of time at 4° C. than possible by conventional process while maintaining suitability of such stored RBCs for transfusion in humans.

Other objects and advantages will become apparent as the description of the invention proceeds.

DETAILED DESCRIPTION OF THE INVENTION

These and other objects, features and many of the attendant advantages of the invention will be better understood upon a reading of the following detailed description when considered in connection with the accompanying drawings wherein:

FIG. 2 shows percent in vivo survival of human RBCs after storage at various time intervals at 4° C. in different suspending media.

Figure 1:
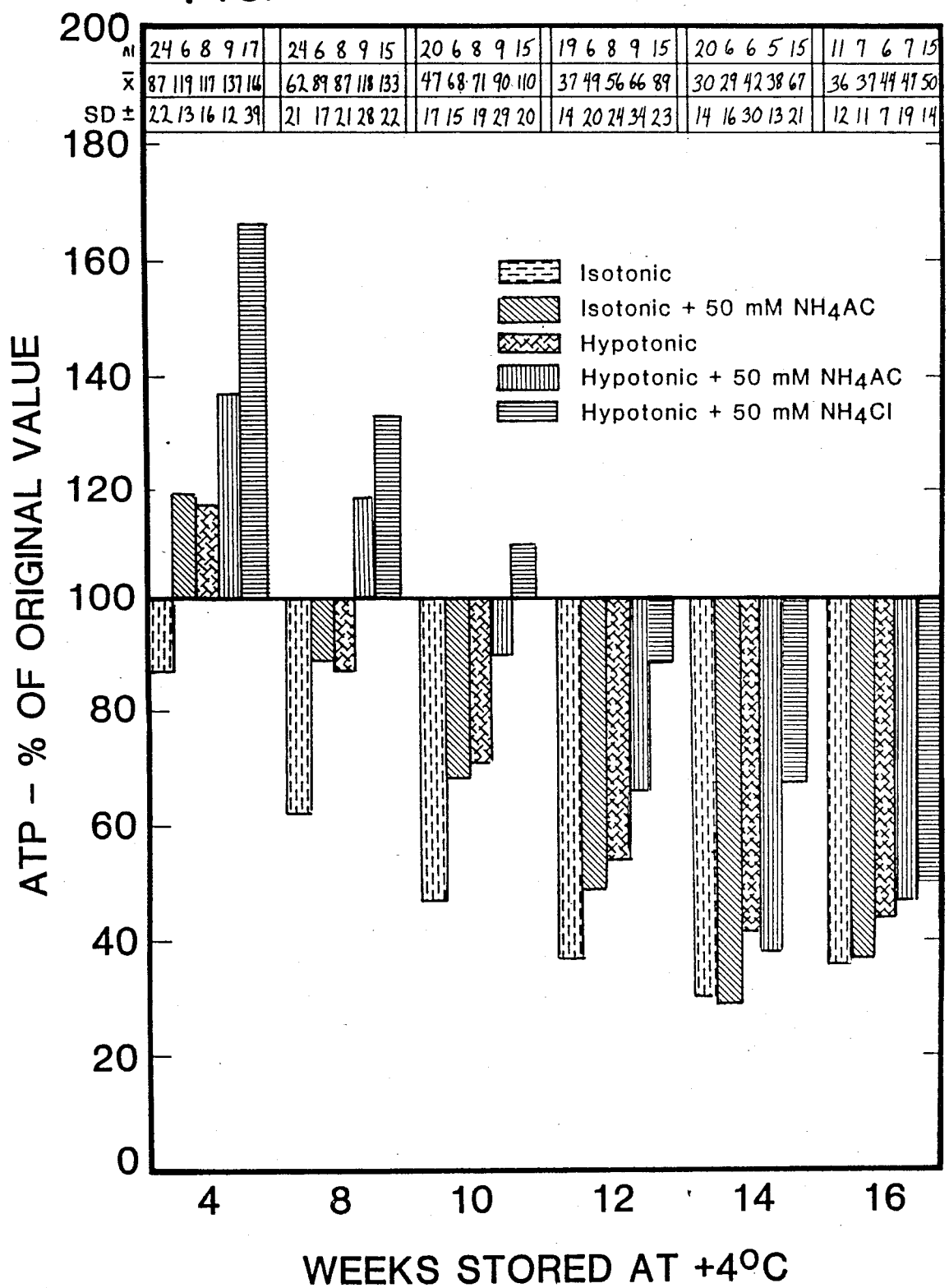
FIG. 1 shows ATP content in human RBCs (percent of original value) as a function of storage time at 4° C. in various suspending media.

Without being bound to any particular theory or explanation, it is postulated that in order to forestall the development of undesirable spicules in the RBCs during refrigerated storage in conventional suspension media, increasing the surface tension of the cells by osmotic swelling may be necessary. The cells are, therefore, suspended in a medium of about 180-220 mOsm (milli-osmolar), more particularly in a medium of about 200 mOsm. The pH of the suspension medium is maintained in a range of about 6.8 to 7.2, preferably around 7.0. Since this involves a reduction in ionic concentration which could lead to an increase in membrane permeability, normal ionic concentration of the cells is maintained by a unique composition employing certain penetrating, ionizable salts in the suspension medium, preferable among such salts being ammonium acetate and ammonium chloride at about 10-200 mM concentration, preferably at about 50 mM concentration. Of course, suitable cations other than ammonium and suitable anions other than acetate and chloride could also be advantageously utilized so long as such salts meet the criteria and objects of the present invention. An example of such salt is methyl amine hydrochloride. The other constituents of the suspending medium are those conventionally used and comprise potassium phosphate, mannitol, adenine, bovine serum albumin, inosine, pyruvate, potassium citrate and glucose at suitable concentrations, for instance the concentration of glucose could be about 80-150 mM, mannitol about 30-80 mM, potassium citrate about 6-90 mM, adenine about 1-5 mM. Mono and dibasic potassium phosphate concentration is adjusted to maintain the pH at about 6.8 to 7.2 of the suspension medium at about 180-220 mOsm.

The term "substantially prolonged" or "extended" storage and the like simply means that viable preservation or storage of RBCs for a period of time greater than that possible by utilizing heretofore known blood bank procedure and conventional suspending media is obtained.

DESCRIPTION OF SPECIFIC EMBODIMENT

A typical composition of the suspending medium in accordance with the present invention comprises an aqueous solution containing:

| | |
|---|---|
| glucose | 110 mM |
| mannitol | 55 mM |
| potassium citrate | 7.9 mM |
| potassium phosphate dibasic | 25.8 mM |
| potassium phosphate monobasic | 14.7 mM |
| adenine | 2 mM |
| ammonium chloride | 50 mM |

Other such compositions can be easily prepared so long as the pH is about 7.0 and the osmolarity is in the range of about 200 mOsm.

Red cells which have been separated from their plasma in the normal course of component manufacture are resuspended in an approximately equal volume of this suspending medium. The cell suspension is then stored at about 4°±2° C. according to standard blood bank procedure which is described in "Clinical Practice of Blood Transfusion" editors: Petz & Swisher, Churchill-Livingston publishers, N.Y., 1981, which is incorporated herein by reference. Chapter 11, page 281 of the reference shows viability data of preserved RBCs by conventional techniques.

When stored in a suspension medium in accordance with the present invention, there is a progressive increase in adenosine triphosphate (ATP) over the first four to five weeks of storage. ATP levels tend to be correlated with red cell survival following transfusion. At four weeks the ATP levels range from 115% to as high as 250% with an average of 165% of the initial value. The ATP level then falls steadily with further storage, reaching the original value at around eleven weeks and falling to 50% of original value at approximately sixteen weeks.

Table 1 shows various components and solute concentrations of suspension media in which red cells were stored for up to 16 weeks. It should be noted that solution #20, which is the preferred suspending medium in accordance with the present invention, maintains red cell ATP at a higher level for a longer time than any other solution tested as shown by FIG. 1.

benefits from both the hypotonicity and the addition of ammonium salts. The benefits of hypotonicity may be associated with the postponement of spicule formation but the reasons for increase in ATP levels is unknown. The mechanism by which the ammonium salts of the present invention when incorporated in the suspension medium increase ATP is also unknown.

FIG. 2 demonstrates the 24 hour in vivo survival figures for red cells stored in solution (c) for periods ranging up to 125 days.

It may be noted that it is unlikely that a hypotonic cell suspension containing ammonium chloride would be acceptable for transfusion. Therefore, it is recommended that, prior to transfusion, the cells should be sedimented by centrifugation and the cells resuspended in a transfusable solution and then transfused.

The hemolysis of RBCs stored in accordance with the present invention is from about 0.3 to 3.8%.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A suspension medium for prolonged storage of red blood cells at about 4° C. consisting essentially of an

TABLE I

Solutions for +4° C. red cell storage - mM concentration
Packed cells and soluion mixed 1-1

| 1glucose | 2mannitol | 3K citrate | 4K$_2$HPO$_4$ | 5KH$_2$PO$_4$ | 6adenine | 7inoaine | 8pyruvate | 9NH$_4$ac | 10NH$_4$Cl | 11other | 12 mOsm | 13pH |
|---|---|---|---|---|---|---|---|---|---|---|---|---|
| 55 |  | 74 | 25.8 | 14.7 | 1 | 30 | 30 |  |  |  | 300 | 7 |
|  | 100 | 41.6 | 40 |  | 1 | 30 | 30 |  |  |  | 423 | 8.7 |
|  | 100 | 41.6 | 40 |  | 1 | 30 | 30 |  |  | 8% BSA |  |  |
|  | 100 | 41.6 | 40 |  | 1 | 30 | 30 |  |  | 2% DMSO |  |  |
| 55 | 55 | 58.6 | 25.8 | 14.7 | 1 | 30 | 30 |  |  |  | 310 | 7.1 |
| 55 | 55 | 58.6 | 25.8 | 14.7 | 1 | 30 | 30 |  |  | 8% BSA |  |  |
| 110 | 55 | 58.6 | 25.8 | 14.7 | 2 |  |  |  |  |  | 310 | 7.1 |
| 110 | 55 | 58.6 | 25.8 | 14.7 | 2 |  |  |  |  | .05 mg insulin | 310 | 7.1 |
| 110 | 55 | 58.6 | 25.8 | 14.7 | 2 | 30 |  |  |  |  | 310 | 7.1 |
| 110 | 55 | 58.6 | 25.8 | 14.7 | 2 | 30 | 30 |  |  |  | 310 | 7.1 |
| 110 | 55 | 58.6 | 25.8 | 14.7 | 2 | 30 | 30 |  |  | 6% PVP |  | 7.1 |
| 110 | 55 | 7.9 | 25.8 | 14.7 | 2 |  |  |  |  |  | 210 | 7.1 |
| 110 | 55 | 7.9 | 25.8 | 14.7 | 2 |  |  | 50 |  |  | 210 | 7.1 |
| 110 | 55 | 58.6 | 25.8 | 14.7 | 2 |  |  | 50 |  |  | 210 | 7.1 |
| 110 | 55 | 58.6 | 25.8 | 14.7 | 2 |  |  | 250 |  |  | 310 | 7.1 |
| 110 | 55 | 58.6 | 25.8 | 14.7 | 2 |  |  | 500 |  |  | 310 | 7.1 |
| 110 | 55 | 58.6 | 25.8 | 14.7 | 2 |  |  | 100 |  |  | 310 | 7.1 |
| 110 | 55 | 58.6 | 25.8 | 14.7 | 2 |  |  | 150 |  |  | 310 | 7.1 |
| 110 | 55 | 7.9 | 25.8 | 14.7 | 2 |  |  | 100 |  |  | 210 | 7.1 |
| 110 | 55 | 7.9 | 25.8 | 14.7 | 2 |  |  |  | 50 |  | 210 | 7.1 |
| 110 |  |  | 63 | 33 | 2 |  |  |  |  |  | 210 | 7.1 |
| 110 | 55 | 7.9 | 16 | 24 | 2 |  |  |  | 50 |  | 210 | 6.6 |
| 110 | 55 | 79 | 25.8 | 14.7 | 2 |  |  |  | 50 | 600 approx | 7.1 |
| 110 | 55 | 7.9 | 25.8 | 14.7 | 2 |  |  |  | 25 |  | 210 | 7.1 |
| 110 | 55 | 7.9 | 25.8 | 14.7 | 2 |  |  |  | 100 |  | 210 | 7.1 |
| 110 | 55 | 7.9 | 25.8 | 14.7 | 2 |  |  |  | 200 |  | 210 | 7.1 |

FIG. 1 shows ATP values at 4, 8, 10, 12, 14 and 16 weeks for cells suspended in (a) an isotonic potassium citrate, phosphate, mannitol, glucose, adenine solution, corresponding to solution #7 in Table 1; (b) the same solution as (a) with ammonium acetate added, corresponding to solution #14 in Table 1; (c) the same solution as (a) with some potassium citrate removed to make it hypotonic, corresponding to solution #12 in Table 1; (d) the same hypotonic solution as (c) with the addition of ammonium acetate, corresponding to solution #13 in Table 1; (e) the same hypotonic solution as (c) with the addition of ammonium chloride, corresponding to solution #20 in Table 1. The results indicate that there are aqueous solution containing about 80–150 mM glucose, 30–80 mM mannitol, 6–90 mM potassium citrate, 1–5 mM adenine and 40–95 mM of a phosphate salt, said solution having an osmolarity of about 180–220 milliosmolar and having 10–200 mM of a penetrating salt, the pH of said solution being about 6.8 to 7.2 wherein said red blood cells can be viably stored.

2. A method of preserving red blood cells for extended period of time at about 4° C. comprising suspending said cells in an aqueous solution consisting essentially of about 80–150 mM glucose, 30–80 mM mannitol, 6–90 mM potassium citrate, 1–5 mM adenine and 40–95 mM of a phosphate salt, said solution having an osmolarity of about 180–220 milli-osmolar and having 10–200 mM of a penetrating salt, the pH of said solution being about 6.8 to 7.2 allowing viable storage of said red blood cells.

3. The suspension medium of claim 1 wherein said penetrating salt is selected from the group consisting of ammonium chloride and ammonium acetate.

4. The suspension medium of claim 3 containing about 110 mM glucose, 55 mM mannitol, 7.9 mM potassium citrate, 2 mM adenine and 50 mM ammonium chloride or acetate.

5. The suspension medium of claim 4 wherein the pH is maintained at a value of about 7.0 by adjusting the pH with suitable amounts of mono or dibasic potassium phosphate.

6. The suspension medium of claim 5 wherein the osmolarity is about 200 mOsm.

7. The method of claim 2 wherein said penetrating salt is selected from the group consisting of ammonium chloride and ammonium acetate.

8. The method of claim 7 containing about 110 mM glucose, 55 mM mannitol, 7.9 mM potassium citrate, 2 mM adenine and 50 mM ammonium chloride or acetate.

9. The method of claim 8 wherein the pH is maintained at a value of about 7.0 by adjusting the pH with suitable amounts of mono or dibasic potassium phosphate.

10. The method of claim 9 wherein the osmolarity is about 200 mOsm.

* * * * *